United States Patent [19]

Lalezari et al.

[11] Patent Number: 4,734,275
[45] Date of Patent: Mar. 29, 1988

[54] ANTI-CURARE AGENTS

[75] Inventors: Iraj Lalezari, Scarsdale; Francis F. Foldes, Briarcliff Manor, both of N.Y.

[73] Assignee: Research Corporation, New York, N.Y.

[21] Appl. No.: 855,053

[22] Filed: Apr. 22, 1986

Related U.S. Application Data

[63] Continuation-in-part of Ser. No. 524,843, Aug. 19, 1983, abandoned.

[51] Int. Cl.$^4$ .............................................. A61K 31/44
[52] U.S. Cl. .................................. 424/10; 514/353
[58] Field of Search .................. 514/353; 546/306; 424/10

[56] References Cited

U.S. PATENT DOCUMENTS

| | | | |
|---|---|---|---|
| 2,344,934 | 2/1943 | West | 546/332 |
| 2,972,528 | 2/1961 | Brian et al. | 546/321 |
| 3,074,955 | 1/1963 | Seymour et al. | 546/332 |
| 3,084,192 | 4/1963 | Smathers | 71/121 |
| 3,293,257 | 12/1966 | Woods et al. | 546/306 |
| 3,330,641 | 7/1967 | Woods et al. | 546/306 |
| 3,932,427 | 1/1976 | Durant et al. | 546/306 |
| 4,149,872 | 4/1979 | Pilgram | 546/306 |
| 4,203,988 | 5/1980 | Bolhofer et al. | 544/131 |
| 4,215,125 | 7/1980 | Durant et al. | 514/332 |
| 4,244,950 | 1/1981 | DeRidder et al. | 514/229 |
| 4,279,639 | 7/1981 | Okamoto et al. | 546/306 |
| 4,281,003 | 7/1981 | Miesel | 546/306 |
| 4,289,765 | 9/1981 | Greve et al. | 514/211 |

OTHER PUBLICATIONS

Bowman et al., Pharmacological Actions of Aminopyridines and Related Compounds, Reviews in Pure and Applied Pharmacological Science, vol. 2, 317–371 (1981).

Den Hertog et al., CA 100 61641q, 1984.

*Primary Examiner*—Jane T. Fan
*Attorney, Agent, or Firm*—Scully, Scott, Murphy & Presser

[57] ABSTRACT

This invention relates to a method for antagonizing induced the neuromuscular blocking effects of certain therapeutic agents and pathological disorders in mammals, which comprises administering to said mammal an antagonizing-effective amount of a compound of the formula:

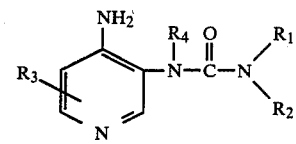

wherein $R_1$ and $R_2$ are each hydrogen, alkyl, alkenyl, alkynyl, aryl, aralkyl, cycloalkyl, cycloalkyl-lower alkyl or hydroxyalkyl, or, when taken together, form a heterocyclic ring with the nitrogen to which they are attached, with the proviso that both are not hydrogen;

$R_3$ is hydrogen or alkyl; and $R_4$ is hydrogen, alkyl, alkenyl, alkynyl, halogen or acyl; or a salt thereof with acids.

28 Claims, No Drawings

ANTI-CURARE AGENTS

RELATED APPLICATIONS

This application is a continuation-in-part of copending U.S. Ser. No. 524,843, filed Aug. 19, 1983 now abandoned.

FIELD OF THE INVENTION

This invention relates to the use of aminopyridine derivatives, more specifically new aminopyridine-substituted ureas, as therapeutic agents capable of antagonizing neuromuscular blocking effects of certain chemical agents and disease states.

BACKGROUND OF THE INVENTION

Certain substituted ureas, and related compounds, the aminopyridines, have been demonstrated as having a wide variety of practical applications. For example, U.S. Pat. No. 2,344,934 describes quarternary nitrogen condensation products of methylol urea ethers which are useful in creaseproofing and waterproofing textile fibers. A wide range of related compounds such as dipyridyl derivatives (U.S. Pat. No. 2,973,528), alpha-halo-formamidines (U.S. Pat. No. 3,084,192), 3-aminopyridines (U.S. Pat. No. 3,547,935), amidines (U.S. Pat. No. 3,074,955), and pyridyl ureas (U.S. Pat. Nos. 3,293,257; 3,330,641) have proven useful as herbicides or plant growth regulators.

Similar compounds have also proven to have many pharmaceutical applications. Pyridyl ureas may be useful as histamine receptor inhibitors (U.S. Pat. Nos. 3,932,427; 4,215,125) or gastric secretion inhibitors (U.S. Pat. No. 4,203,988). Certain other pyridine derivatives exhibit diuretic activities (U.S. Pat. No. 4,244,950) or broncho-spasmolytic action (U.S. Pat. No. 4,289,765).

Of particular interest are the aminopyridines which show a wide variety of neural effects, such as facilitating chemical transmission at central synapses, autonomic ganglia and neuromuscular junctions. Certain of these compounds may also be utilized in effecting conduction in excitable membranes and increasing muscle contractibility (Bowman and Savage, Rev. in Pure and Appl. Pharmacol. Sci., 2:317, 1981). Among the most important of the practical applications of this activity is their potential use as anti-curare agents.

In practice, nondepolarizing compounds such as curare and its derivatives, for example, d-tubocurarine and pancuronium are routinely utilized to achieve muscular relaxation during surgery. Antagonism of the neuromuscular block effected by these curare compounds has generally been accomplished by the administration of anticholinesterases such as neostigmine methylsulfate (Prostigmine) or pyridostigmine bromide (Mestinon). Unfortunately, anticholinesterases generally cause such undesirable muscarinic side effects as cardiac arrhythmias, bradycardia, atrio-ventricular block, bronchiolar constriction and increased intestinal motility, and must be administered simultaneously with antimuscarinic (anticholinergic) agents such as atropine sulfate or glycopyrrolate. Additionally, anticholinesterases have no antagonistic effect on the neuromuscular blocks effected by certain antibiotics, such as aminoglycosides, lincomycin, spectinomycin and polypeptide-type antibiotics, local anesthetics, low $Ca^{++}$ or high $Mg^{++}$ concentration in extracellular fluid or botulinum poisoning.

Availability of a compound with potential for broad application as a neuromuscular block antagonist, and which also has none of the unpleasant anticholinesterase side effects, is clearly desirable. Aminopyridines, and in particular, 4-aminopyridine (4-AP), have no anticholinesterase activity and have been shown to not only reverse the side effects of clinically used muscle relaxants, but also antagonize the effects of the other neuromuscular blocks listed above (Bowman and Savage, Rev. in Pure and Appl. Pharmacol. Sci. 2:317, 1981; Agoston, et al., Br. J. Anaesth. 50:383, 1978). Unfortunately, the use of 4-AP is accompanied by such undesirable side effects as elevated blood pressure, anxiety, insomnia, and a level of central nervous system stimulation which may manifest itself ultimately in convulsions. Therefore, its utility as a therapeutic agent is clearly very limited (Marshall, Advances in the Biosciences 35:145, 1982).

Surprisingly, recent experimentation has shown that certain aminopyridine derivatives, in particular, substituted ureas, exhibit potency as neuromuscular block antagonists equivalent to or even greater than that of known aminopyridines. These compounds, similarly to 4-AP, do not require concurrent use of anticholinergic drugs which may have the above-mentioned dangerous side effects. The compounds of the present invention also represent a significant improvement over previous compounds in that they do not exhibit the unpleasant, an often lethal, central nervous system side effects which may accompany administration of substances such as 4-AP.

BRIEF DESCRIPTION OF THE INVENTION

The subject of the present invention is a method of antagonizing neuromuscular blocking effects in a mammal which comprises administering to said mammal an antagonistic effective amount of a compound of the formula:

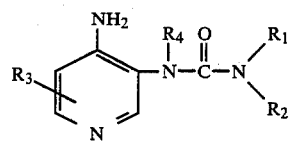

wherein $R_1$ and $R_2$ are each hydrogen, alkyl, alkenyl, alkynyl, aryl, aralkyl, cycloalkyl, cycloalkyl-lower alkyl, or hydroxylalkyl, or when taken together, form a nitrogen-heterocyclic ring with the nitrogen to which they are attached, with the proviso that both are not hydrogen;

$R_3$ is hydrogen or lower alkyl; and $R_4$ is hydrogen, or lower alkyl, lower alkenyl, lower alkynyl, halogen or acyl and salts thereof with acids.

The alkyl groups in alkyl per se and in aralkyl, cycloalkyl-lower alkyl and carbalkoxy contain from 1 to 6 carbon atoms; thus the alkyl groups may be methyl, ethyl, propyl, butyl, pentyl or hexyl.

The cycloalkyl groups in cycloalkyl per se and cycloalkyl-lower alkyl contain from 4 to 8 carbon atoms.

The acyl group is preferably alkanoyl, containing from 1 to 6 carbon atoms, and includes, e.g., acetyl and propionyl.

The alkenyl and alkynyl groups may be straight-chained or branched and contain from 2 to 6 carbon atoms, e.g., allyl, butenyl, pentenyl, hexenyl, butynyl, propynyl, pentynyl and the like.

The aryl groups contain from 6 to 10 carbon atoms and include phenyl, tolyl and naphthyl.

The halogen may be fluoro, bromo, iodo or chloro, and is preferably bromo.

The nitrogen-heterocyclic ring includes any 5 or 6-membered ring, such as pyridine, pyrrole, pyrrolidine, morpholine, piperidine or piperazine.

The particularly preferred compounds of the invention are those in which $R_1$ and $R_2$ are each alkyl, aryl, aralkyl or nitrogen-heterocyclic, and $R_3$ and $R_4$ are each hydrogen.

DETAILED DESCRIPTION OF THE INVENTION

The therapeutic compounds of the present invention may generally be manufactured by reacting a compound of the general formula:

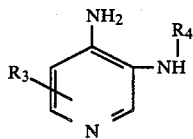

with a substituted carbamoyl chloride of the general formula:

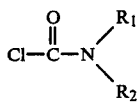

wherein $R_1$, $R_2$, $R_3$ and $R_4$ have the same meanings as stated above.

Such carbamoyl chlorides are well-known intermediates which can be prepared, for example, by the reaction of phosphorus pentachloride and oxalic acid monoamide in chloroform, or by the reaction of phosgene and mono- or disubstituted amines.

The reaction is carried out under refluxing conditions, in the presence of any suitable organic solvent. Illustrative of such solvents are halogenated hydrocarbons, such and dichloroethane, chloroform or carbon tetrachloride. After cooling, the organic layer is separated, and the residue extracted with several washings of isopropanol. Purification of the compound is accomplished by passing through a silica gel column, elution with isopropanol, and evaporation of the solvents.

The present aminopyrdridine derivatives are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present compounds. Therefore, all acid salts of the present compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the products.

In addition to the effectiveness of the aminopyridine derivatives as anti-curare agents, these compounds are also useful in treatment of other types of disorders resulting from the effects of neuromuscular blocking. For example, certain antibiotics, such as aminoglycosides or polypeptides, administered either alone, or in conjunction with muscle relaxants, may cause neuromuscular block in surgical patients; these blocks cannot be removed by anticholinesterases. Similarly, magnesium, which is frequently used for treatment of ecclampsia, can cause a neuromuscular block, either on its own or in combination with muscle relaxants. Botulium A intoxication also causes a neuromuscular block which is effectively removed by administration of the present compounds; this is particularly significant in that there is no effective treatment of this condition which causes death by paralysis of respiratory muscles.

Treatment of the symptoms of carcinomatous neuropathy (Eaton-Lambert Syndrome) may also be achieved with the aminopyridine derivatives. This condition is an occasional complication of bronchogenic or other types of carcinoma. Myasthenia gravis, which is often treated with anticholinesterases, may also be treated in the present manner. The present compounds have considerable anticholinesterase activity, but additionally increase the presynaptic release of acetylcholine, thus increasing the force of contraction of still functioning muscle fibers. Other conditions, such as multiple sclerosis, which generally cause muscle weakness, may also be so treated. Also, in connection with its anticholinesterase activity, the present compounds may be effectively employed to alleviate symptoms of senile dementia of the Altzheimers's type, which is currently believed to be caused by the inhibition of synthesis and release of acetylcholine in specific brain areas. Although technically not a "neuromuscular" block, this condition is included, for purposes of the present specification and claims, among these disorders because of the similarity of the physiological response involved. The present compounds increase release of acetylcholine, and inhibit the enzymatic breakdown of that chemical.

The mode of administration and dosage ranges vary depending upon the condition to be treated. For treatment of curare-, antibiotic-, or magnesium- induced neuromuscular blocks, administration of the compounds is parenteral, i.e., intravenous, intraperitoneal, intramuscular, or subcutaneous. Effective dosages are in the range of about 0.1-2.0 mg/kg, with the preferred range being about 0.2 to 1.0 mg/kg, by intravenous administration. Similar dosages, in intravenous administration, may be employed for emergency relief of symptoms of Eaton-Lambert Syndrome or myasthenia gravis. For more routine symptomatic treatment of these two conditions, the compounds may be administered orally in capsules that dissolve in the duodenum or other parts of the intestine, or by rectal suppository. In these non-parenteral routes of administration, the dosage range is generally 0.3 to 6.0 mg/kg, and preferably 0.6 to 3.0 mg/kg.

The process of the present invention may be better understood with reference to the following example, which is provided for the purpose of illustration and should not be considered as limiting the scope of the invention.

For treatment of botulinum A intoxication, treatment is achieved by continuous intravenous infusion of a 0.1 to 2.0 mg/ml (w/v) solution. The effective dosage is about 0.1 to 2.0 mg/kg/hour preferably about 0.2 to 1.0 mg/kg hour.

Treatment of senile dementia can be accomplished by oral administration of from about 0.1 to 3.0 mg/kg, preferably about 0.2 to 1.0 mg/kg.

For treatment of multiple sclerosis and related disorders, intravenous administration may be accomplished as in treatment of curare-induced neuromuscular block; treatment may also be achieved orally or rectally as described above.

For parenteral administration, the compounds may be used alone or in combination with any commonly used pharmaceutically acceptable carrier vehicle, such as isotonic saline. For oral or rectal administration, the compounds are formulated into capsule or suppository form by any of the methods which are routinely used in the art for this purpose.

The particularly preferred therapeutic agent for the present purposes is the novel compound LF-14 (1,1-dimethyl-3-(4-amino-3-pyridyl) urea. The method of the present invention is applicable to treatment of any mammal, especially humans.

EXAMPLE 1

1,1-Dimethyl-3-(4-amino-3-pyridyl)-urea (LF-14)

A mixture of 0.218 g (2 mmoles) of 3,4-diaminopyridine, 0.215 g (2 mmoles) of dimethyl carbamoyl chloride, and 0.822 g (6 mmoles) of anhydrous potassium carbonate, in 60 ml of 1,2-dichloroethane, was refluxed for 15 hours. After cooling, the solvent was evaporated in a rotary evaporator, leaving a gummy material. The residue was then extracted with a total of 60 ml of hot isopropanol.

The resulting isopropanol solution was charcoaled, then passed through a short column of silica gel. The column was then washed with 10 ml of isopropanol. Subsequent evaporation of the solvent yielded a colorless, crystalline, extremely hygroscopic material. The yield was 90%, or 325 mg. The purity of the compound was checked by thin layer chromatogrpahy, and the structure was confirmed by NMR spectroscopy and chemical analysis.

Utilizing the techniques described, above the following compounds may also be made:

| $R_1$ | $R_2$ | $R_3$ | $R_4$ |
|---|---|---|---|
| carbethoxy | H | H | H |
| phenyl | H | methyl | H |
| methyl | cyclopentyl | H | H |
| butenyl | methyl | H | H |
| cyclopentylmethyl | methyl | H | H |
| methyl | methyl | H | methyl |
| benzyl | methyl | methyl | H |
| ethyl | ethyl | H | ethyl |
| acetyl | methyl | H | H |
| H | propynyl | methyl | H |
| propynyl | methyl | H | H |
|  | pyrridyl | H | H |
|  | pyrrolidyl | H | H |

The superiority of the compounds of the present invention over previously known compounds has been demonstrated experimentally. Experiments were conducted to test both the neuromuscular potency and central nervous system effects of the aminopyridine-substituted ureas 1,1-dimethyl-3-(4-amino-3-pyridyl)-urea (LF-14, the compound of Example 1) and 1,1-dimethyl-(3,4-pyridyl)-urea (LF-10; Foldes, et al., Anesthesiology 57:A273, 1982). Comparisons were made with two other aminopyridines: 4-aminopyridine (4-AP) and 3,4-diaminopyridine (3,4-DAP).

Thus, it has been demonstrated that, when testing the ability of each compound to antagonize neuromuscular blocks induced by curare, LF-14 has a molar potency 17 times that of 4-AP in vitro, and 9 times that of 4-AP in vivo (Table I). Similarly, when testing the potential for causing undesirable central nervous sytem side effects, LF-14 exhibited no stimulatory effects on the central nervous system (Table II). Further details of the testing procedures are described in the following examples.

EXAMPLE 2

In in vitro tests to determine neuromuscular potency, phrenic nerve-hemidiaphragm preparations from male Sprague-Dawley rats were suspended in modified Krebs solution. In vivo experiments focused on the sciatic nerve-tibialis anterior muscle preparations in male Sprague-Dawley rats. In each case, stimulation of nerves was accomplished via bipolar platinum electrodes, with supramaximal impulses of 0.2 msec duration at 0.1 HZ, and the isometric twitches were continuously recorded. Greater than 90 % steady state neuromuscular block was achieved either by addition of appropriate concentrations (in vitro) or continuous i.v. infusions (in vivo) of either d-tubocurarine or pancuronium. Antagonism of the induced neuromuscular block was accomplished by the addition of increments of 4-AP, 3,4-DAP, LF-10 or LF-14. The antagonist ED50 of the compounds summarized in Table I clearly show that although all tested compounds antagonize the neuromuscular effects of nondepolarizing muscle relaxants, on a molar basis the neuromuscular potency of LF-14 was greatest both in vitro and in vivo.

TABLE I

Antagonism of the neuromuscular block by 4- and 3,4-disubstituted pyridine derivatives in rats

| Muscle Relaxant | Antagonist | ED 50 of Antagonists** | | Relative Molar Potency | |
|---|---|---|---|---|---|
|  |  | In Vitro (nmol/min) | In Vivo (mg/Kg) | In Vitro | In Vivo |
| d-Tubocurarine | 4-Aminopyridine | 1.7 + 0.10* | 0.17 + 0.01 | 1.0 | 1.0 |
|  | 3,4-Diaminopyridine | 0.8 + 0.05 | 0.12 + 0.02 | 2.1 | 1.6 |
|  | #LF-10 | 0.4 + 0.06 | 0.09 + 0.00 | 4.3 | 7.5 |

TABLE I-continued

Antagonism of the neuromuscular block by 4- and 3,4-disubstituted pyridine derivatives in rats

| Muscle Relaxant | Antagonist | ED 50 of Antagonists** | | Relative Molar Potency | |
|---|---|---|---|---|---|
| | | In Vitro (nmol/min) | In Vivo (mg/Kg) | In Vitro | In Vivo |
| Pancuronium | ##LF-14 | 0.1 + 0.01 | 0.04 + 0.00 | 17 | 9 |
| | 4-Aminopyridine | 2.6 + 0.33 | 0.13 + 0.01 | 1.0 | 1.0 |
| | 3,4-Diaminopyridine | 0.9 + 0.02 | 0.18 + 0.03 | 2.7 | 0.8 |
| | LF-10 | 0.5 + 0.07 | 0.13 + 0.00 | 3.4 | 2.3 |
| | LF-14 | 0.1 + 0.01 | 0.04 + 0.00 | 17 | 8.2 |

*All values represent means + SEM of 4 experiments
**The concentration in vitro or the i.v. dose that will increase twitch tension to 50% of control in the presence of the concentration or dose of muscle relaxant that caused a >90% steady state block.
1,1-dimethyl-(3,4-pyridyl)-urea
1,1-dimethyl-3-(4-amino-3-pyridyl)-urea

EXAMPLE 3

Tests were conducted to determine the stimulatory effects of the compounds of the present invention upon the central nervous system. Male Sprague-Dawley rats were injected subcutaneously with 35 mg/kg of pentobarbital alone, or together with 1.1 mg/kg of LF-10 or LF-14, or 1.5 mg/kg of 4-AP or 3,4-DAP (Foldes, et al., Anesthesiology 57:A-273, 1982). The time of onset and duration of the loss of righting reflex (LRR) was observed. The results of these tests is presented in Table II.

TABLE II

Central effects of pyridines (after Foldes, et al., 1982)

| Compound | Loss of righting reflex | |
|---|---|---|
| | Onset (Min.) | Duration (min.) |
| Control | 11.4* | 71.9 |
| 4-Aminopyridine | 15.2# | 42.0 |
| LF-10 | 14.8 | 63.7 |
| 3,4-Diaminopyridine | 13.3+ | 78.9 |
| LF-14 | 12.4 | 75.7 |

*Mean + SEM of number
+p < 0.05
p < 0.001 (Student's t test)

These data showed that while LF-10 exhibited some effect on shortening the duration of LRR caused by pentobarbital administration, LF-14 had substantially no effect on the pentobarbital induced LRR. 4-AP is shown to significantly (p<0.001) reduce the central nervous system effects of barbiturates. Therefore, LF-14 and related compounds represent an improvement over previously known aminopyridines in both their neuromuscular potency and lack of unwanted stimulatory effects on the central nervous system.

What is claimed is:

1. A method for antagonizing neuromuscular blocking effects induced by therapeutic agents and physiological disorders in mammals, which comprises administering to said mammal an antagonizing-effective amount of a compound of the formula:

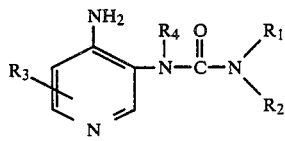

wherein $R_2$ and $R_2$ are each hydrogen, lower alkyl, lower alkenyl, lower alkynyl, aryl, aralkyl, cycloalkyl, cycloalkyl-lower alkyl or hydroxyalkyl, with the proviso that both are not hydrogen;

$R_3$ is hydrogen or lower alkyl; and $R_4$ is hydrogen, lower alkyl, lower alkenyl, lower alkynyl, halogen or acyl; wherein the alkyl groups in alkyl per se, aralkyl, cycloalkyl-lower alkyl and hydroxyalkyl contain from 1 to 6 carbon atoms; the cycloalkyl groups in cycloalkyl per se and cycloalkyl-lower alkyl contain from 4 to 8 carbon atoms; the alkenyl and alkynyl groups contain from 2 to 6 carbon atoms; the acyl group contains from 1 to 6 carbon atoms; and the aryl groups in aryl per se and aralkyl contain from 6 to 10 carbon atoms; or a salt thereof with acid.

2. The method according to claim 1 wherein $R_1$ and $R_2$ are each selected from the group consisting of lower alkyl, aryl, and aralkyl, $R_3$ and $R_4$ are each hydrogen.

3. The method according to claim 2 wherein $R_1$ and $R_2$ are each lower alkyl.

4. The method according to claim 2 wherein $R_1$ and $R_2$ are each methyl.

5. The method of claim 4 wherein the compound is 1,1-diemethyl-3-(4-amino-3-pyridyl) urea.

6. The method of claim 1 wherein the therapeutic agent is selected from the group consisting of a non-depolarizing muscle relaxant, an antibiotic which inhibits neuromuscular transmission and magnesium.

7. The method of claim 6 wherein the muscle relaxant is curare, d-tubocurarine or pancuronium.

8. The method of claim 6 wherein the antibiotic is an aminoglycoside, polypeptide-type antibiotic, lincomycin or spectinomycin.

9. The method of claim 1 wherein the disorder is botulism A.

10. The method of claim 1 wherein the disorder is myasthenia gravis.

11. The method of claim 1 wherein the disorder is Eaton-Lambert Syndrome.

12. The method of claim 1 wherein the disorder is senile dementia (Altzheimer's type).

13. The method of claim 1 wherein the disorder is multiple sclerosis.

14. The method of claim 6 wherein the compound is administered intravenously.

15. The method of claim 14 wherein the compound is administered in an amount of from about 0.1 to 2.0 mg/kg.

16. The method of claim 9 wherein the compound is administered by intravenous infusion of about 0.1 to 2.0 mg/ml solution.

17. The method of claim 10 wherein the compound is administered intravenously, orally or rectally.

18. The method of claim 17 wherein, when administered intravenously, the compound is administered in an amount of from about 0.1-2.0 mg/kg.

19. The method of claim 17 wherein, when administered orally or rectally, the compound is administered in an amount of from about 0.3 to 6.0 mg/kg.

20. The method of claim 11 wherein the compound is administered intravenously, orally or rectally.

21. The method of claim 20 wherein, when administered intravenously, the compound is administered in an amount of from about 0.1 to 2.0 mg/kg.

22. The method of claim 20 wherein, when administered orally or rectally, the compound is present in an amount of from about 0.3-6.0 mg/kg.

23. The method of claim 12 wherein the compound is administered orally.

24. The method of claim 23 wherein the compound is in an amount of about 0.1 to 3.0 mg/kg.

25. The method of claim 13 wherein the compound is administered intravenously, orally or rectally.

26. The method of claim 25 wherein, when administered intravenously, the compound is administered in an amount of from about 0.1 to 2.0 mg/kg.

27. The method of claim 25 wherein, when administered orally or rectally, the compound is administered in an amount of from about 0.3 to 6.0 mg/kg.

28. A therapeutic composition for the antagonism of neuromuscular block which comprises a compound of the formula:

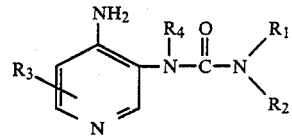

at a unit dosage level of from about 0.1 to about 6.0 mg/kg. wherein $R_1$ and $R_2$ are each hydrogen, lower alkyl, lower alkenyl, lower alkynyl, aryl, aralkyl, cycloalkyl, cycloalkyl-lower alkyl or hydroxyalkyl, with the proviso that both are not hydrogen;

$R_3$ is hydrogen or alkyl; and $R_4$ is hydrogen, lower alkyl, lower alkenyl, lower alkynyl, or halogen or acyl; wherein the alkyl groups in alkyl per se, aralkyl, cycloalkyl-lower alkyl and hydroxyalkyl contain from 1 to 6 carbon atoms; the cycloalkyl groups in cycloalkyl per se and cycloalkyl-lower alkyl contain from 4 to 8 carbon atoms; the alkenyl and alkynyl groups contain from 2 to 6 carbon atoms; the acyl group contains from 1-6 carbon atoms and the aryl groups in aryl per se and aralkyl contain from 6 to 10 carbon atoms;

or a salt thereof with acid.

* * * * *